(12) United States Patent
Perrin et al.

(10) Patent No.: US 11,660,324 B2
(45) Date of Patent: May 30, 2023

(54) COPPER COMPLEXES FOR TREATMENT OF NEURODEGENERATIVE DISORDERS

(71) Applicant: ALS Therapy Development Institute, Cambridge, MA (US)

(72) Inventors: Steven Perrin, Newbury, MA (US); Fernando G. Vieira, Newton, MA (US); Alan Gill, Reading, MA (US); Theo Hatzipetros, Belmont, MA (US); Kyle Denton, Medford, MA (US); Matvey Lukashev, Upton, MA (US)

(73) Assignee: ALS THERAPY DEVELOPMENT INSTITUTE, Cambridge, MA (US)

( * ) Notice: Subject to any disclaimer, the term of this patent is extended or adjusted under 35 U.S.C. 154(b) by 338 days.

(21) Appl. No.: 16/938,114

(22) Filed: Jul. 24, 2020

(65) Prior Publication Data

US 2021/0038676 A1  Feb. 11, 2021

Related U.S. Application Data

(60) Provisional application No. 62/878,581, filed on Jul. 25, 2019.

(51) Int. Cl.
| | | |
|---|---|---|
| *A61K 38/00* | (2006.01) | |
| *A61K 38/02* | (2006.01) | |
| *A61P 25/28* | (2006.01) | |
| *A61K 9/16* | (2006.01) | |

(52) U.S. Cl.
CPC ............ *A61K 38/02* (2013.01); *A61K 9/1623* (2013.01); *A61P 25/28* (2018.01)

(58) Field of Classification Search
CPC .... A61K 31/555; A61K 38/02; A61K 9/1623; A61P 25/00; A61P 25/16; A61P 25/28
See application file for complete search history.

(56) References Cited

U.S. PATENT DOCUMENTS

2020/0188430 A1   6/2020  Beckman et al.

FOREIGN PATENT DOCUMENTS

| EP | 2749295 A1 | 7/2014 | |
|---|---|---|---|
| WO | WO 2012/112862 A2 | 8/2012 | |
| WO | 2015/070177 A2 | 5/2015 | |
| WO | WO-2015070177 A2 * | 5/2015 | ............ A61K 33/34 |
| WO | WO-2019046761 A1 * | 3/2019 | ........... A61K 31/155 |

OTHER PUBLICATIONS

International Search Report and Written Opinion for PCT International Patent Application No. PCT/US2020/043479, dated Oct. 21, 2020, 11 pages.
Munakata et al., "Copper-Trafficking efficacy of copper-pyruvaldehyde bis(N4-methylthiosemicarbazone) on the macular mouse, an animal model of Menkes disease", Pediatric Research, Jun. 22, 2012, vol. 72, No. 3, pp. 270-276.
Theme 9 Therapeutic Strategies (2016, Amyotrophic Lateral Sclerosis and Frontotemporal Degeneration, 17: sup 1, 236-263, DOI: 10.1080/21678421.2016.1232064; https://doi.org/10.1080/21678421.2016.1232064.
Meeusen et al., "227—Complex Role of Copper Delivery by CuATSM to Superoxide Dismutase (SOD1) in Mouse Models of ALS", *Free Radical Biology and Medicine* 100(Supplement):S105; https://doi.org/10.1016/j.freeradbiomed.2016.10.268 (Nov. 2016).

* cited by examiner

*Primary Examiner* — Aradhana Sasan
*Assistant Examiner* — Mercy H Sabila
(74) *Attorney, Agent, or Firm* — Brian C. Trinque; Lathrop GPM LLP

(57) ABSTRACT

The present disclosure relates to the use of CuPTSM in methods and compositions for treating subjects with a neurodegenerative disease. Subjects with a neurodegenerative disease can have, e.g., amyotrophic lateral sclerosis (ALS).

14 Claims, 9 Drawing Sheets

COPPER COMPLEXES FOR TREATMENT OF NEURODEGENERATIVE DISORDERS

RELATED APPLICATION

This application claims priority to U.S. Provisional Application No. 62/878,581, filed Jul. 25, 2019. The entire contents of this application are incorporated herein by reference.

BACKGROUND

Neurodegenerative diseases are age-dependent disorders that are becoming increasingly prevalent, in part due to the increasing elderly population (Heemels, *Nature* (2016) 539: 179).

For example, amyotrophic lateral sclerosis (ALS), also known as motor neuron disease, Lou Gehrig's disease, or Charcot's disease, is estimated to affect 30,000 Americans and over 400,000 people worldwide at any given time. Approximately 5,000 Americans are diagnosed with ALS every year. The disease causes the unrelenting death of motor neurons, resulting in a progressive paralysis that kills its victims within one to five years on average. Most people diagnosed with ALS live 3-5 years after their first signs of disease. About 10% of people with ALS survive at least 10 years. The variable rate of disease progression makes prognosis difficult to predict, and therapies challenging to develop.

Only two agents (riluzole and edaravone) have been approved by the FDA for treating ALS, and while both slow disease progression in a subset of patients, and can extend life by up to a few months, neither is able to treat or cure the disease.

Some inherited forms of ALS are caused by genetic mutations. The genetic change alters an abundant enzyme within cells called copper-zinc superoxide dismutase (Cu—Zn superoxide dismutase, now called commonly SOD1). This enzyme serves to keep cells safe from metabolic waste that can cause damage if not rendered harmless.

CuATSM has been shown to be protective in the high expressing superoxide dismutase SOD1$^{G93A}$ mice by the rigorous criteria established in the art. However, the high copper affinity of CuATSM causes this agent to be an inefficient delivery vehicle to bypass the distribution system that naturally limits copper transport into the central nervous system ("CNS").

There is therefore a need in the art for improved therapeutic agents that can treat neurological diseases and/or copper deficiency-related disorders.

SUMMARY

This disclosure provides methods and compositions for the treatment of neurodegenerative disorders in a subject in need thereof. In particular, in one aspect provided herein is a method of treating or preventing neurodegenerative disease in a subject in need thereof, comprising administering to the subject a therapeutically effective amount of copper PTSM (CuPTSM). It has been surprisingly found that CuPTSM is more efficacious than CuATSM for treating symptoms of ALS at significantly lower doses and markedly less in vivo drug exposure.

In various embodiments, treating the subject comprises administering a therapeutically effective amount of copper PTSM (CuPTSM).

In various embodiments, the neurodegenerative disease is amyotrophic lateral sclerosis (ALS), frontal temporal dementia (FTD), Parkinson's disease, Huntington's disease, and Alzheimer's disease.

In various embodiments, the neurodegenerative disease is ALS. In various embodiments, the ALS is familial or sporadic.

In various embodiments, the subject is treatment naïve. In various embodiments, the subject has received previous treatment for ALS.

In various embodiments, the therapeutically effective dose of CuPTSM is 0.01 mg/kg/day to 12 mg/kg/day.

In various embodiments, the subject is human, and the human has a genetic mutation associated with ALS. In various embodiments, the genetic mutation associated with ALS comprises a mutation in the SOD1 gene.

In various embodiments, the CuPTSM is administered to the subject in combination with an additional ALS treatment therapy.

In various embodiments, the CuPTSM is administered at a dose that achieves a plasma Cmax of about 50-640 ng/mL in the subject.

In another aspect, provided herein is a pharmaceutical composition comprising CuPTSM and a pharmaceutically acceptable excipient.

In various embodiments, the pharmaceutically acceptable excipient comprises cellulose and a surfactant. In various embodiments, the cellulose is methylcellulose. In various embodiments, the surfactant is a polysorbate. In various embodiments, the polysorbate is TWEEN-80.

DETAILED DESCRIPTION

Figure 1A:
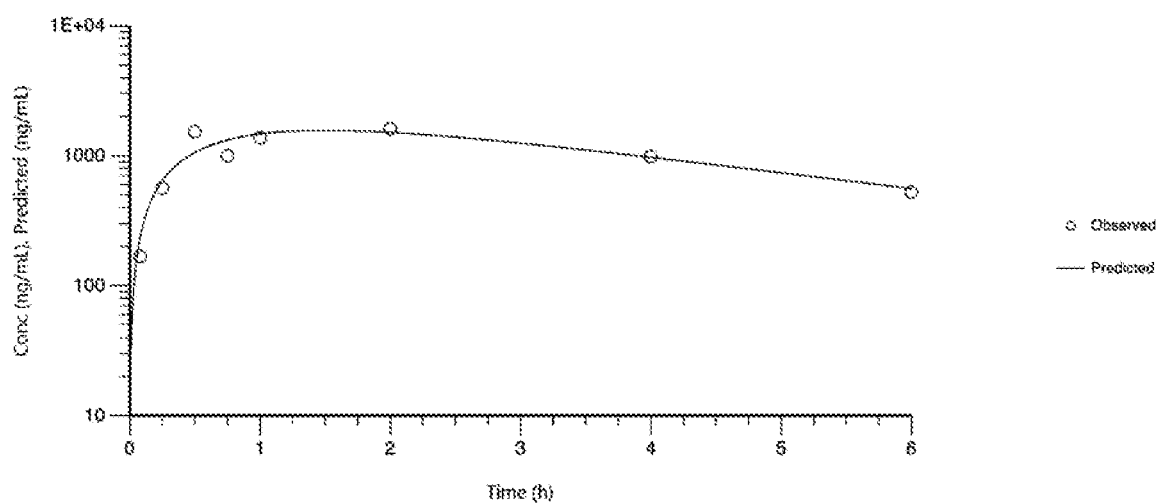
FIG. 1A is a graph depicting the plasma concentrations of CuPTSM over a period of 6 hr after administration of a single dose of 30 mg/kg.

Provided herein are methods of treating a neurodegenerative disease in a subject in need thereof, the method comprising administering to the subject a therapeutically effective amount of CuPTSM. In an embodiment, the neurodegenerative disease is amyotrophic lateral sclerosis (ALS), frontotemporal dementia (FTD), Parkinson's disease, Huntington's disease, and Alzheimer's disease. In an embodiment, the neurodegenerative disease is ALS.

As discussed above, CuATSM has been used clinically for the treatment of ALS, but suffers from significant drawbacks that severely limit its use as a therapeutic agent. Further, CuATSM has a compact, symmetric structure, which contributes to another limitation associated with this compound: its compact structure allows the ATSM ligand component to rapidly form extremely stable crystals, which causes several challenges in making and formulating this compound, hindering its ability to serve as suitable pharmacological agent. For example, the metal-free ATSM ligand component crystallizes within seconds during its synthesis in all common refluxing solvents; thus, it is difficult to subsequently add copper in the final step of the synthesis, particularly at an industrial scale needed to produce the large quantities required for clinical use.

To address these challenges, provided herein is CuPTSM as an effective therapeutic for the treatment of neurodegenerative diseases, including ALS. CuPTSM is an asymmetric copper(II) bis(thiosemicarbazone) complex, in which the bis(thiosemicarbazone) ligand is coordinated to the copper center in a κ⁴ fashion. This compound was first synthesized in 1987 (Int. J. Rad. Appl. Instr., part B, 1987, 14, 59), and has been used as a tracer for positron emission tomography. CuPTSM differs from CuATSM in the symmetry of the ligand backbone (see structures below). It has been surprisingly found that despite the lower drug exposure in vivo of CuPTSM compared to CuATSM, CuPTSM is more efficacious at treating symptoms of ALS at significantly lower dosages.

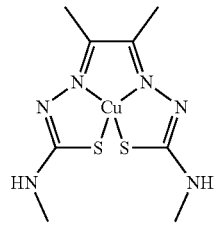

CuATSM

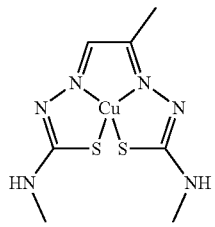

CuPTSM

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including±5%, ±1%, and ±0.1% from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition, and may include, for example, minimal changes or improvements in one or more measurable markers of the disease or condition being treated.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "use" includes any one or more of the following embodiments of the invention, respectively: the use in the treatment of ALS the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In an embodiment, provided herein is the use of CuPTSM for use as a medicament.

As used herein, the term "patient," "individual," or "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from, schizophrenia. In another embodiment, the subject is a cell.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. The term "individual" does not denote a particular age or sex.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The terms "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "sporadic" refers to a neurodegenerative disease, ALS for example, that is not inherited. Sporadic ALS accounts for about 90% of cases, where the affected individual is the only member of the family with the disease. The cause of sporadic ALS is not well understood, but may be due to a combination of environmental and genetic risk factors.

The term "familial" refers to a neurodegenerative disease, ALS for example, that is inherited. Familial ALS accounts for about 10% of cases, where more than one person in the family has ALS and sometimes family members have frontotemporal dementia as well. People with familial ALS often start showing symptoms at earlier ages than in sporadic ALS. Familial ALS is most often autosomal dominant.

"Elimination half-life" is used in the ordinary sense, as in Goodman and Gillman's The Pharmaceutical Basis of Therapeutics (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, t½, the time required for 50% completion of the process. The units of these two constants are time−1 and time, respectively. A first-order rate constant and the half-time of the reaction are simply related (k×t½=0.693) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph. "Absorption half-life" is defined as the amount of time necessary for one-half of a dose of CuPTSM to be absorbed.

Methods of Treatment

The methods described herein comprise administering a therapeutically amount of CuPTSM to a subject in need thereof. A "therapeutically effective amount" is an amount of CuPTSM that, when administered to a patient by itself, effectively treats a neurodegenerative disease. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the CuPTSM that corresponds to a therapeutically effective amount is strongly dependent on the type of disease, stage of the disease, the age of the patient being treated, and other facts.

In an aspect, provided herein is a method of treating or preventing ALS in a subject in need thereof, the method comprising administering to the subject a therapeutically effective amount of CuPTSM.

In another aspect, provided herein is the use of CuPTSM for the manufacture of a medicament for treating ALS in a subject.

In different embodiments, depending on the effective amount of CuPTSM used, the CuPTSM can effectively treat ALS.

In certain embodiments, the therapeutically effective dose of CuPTSM is 0.01 mg/kg/day to 12 mg/kg/day.

In certain embodiments, the dose of CuPTSM for treatment is about, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, or 72 mg. In an embodiment, the dose of CuPTSM for treatment is about, per day, 0.1 mg-72 mg.

In certain embodiments, the dose of CuPTSM for treatment is, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, or 72 mg. In an embodiment, the dose of CuPTSM for treatment is, per day, 0.1 mg-72 mg.

In certain embodiments, the dose of CuPTSM for treatment is about, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, or 64 mg. In an embodiment, the dose of CuPTSM for treatment is about, per day, 0.1 mg-64 mg.

In certain embodiments, the dose of CuPTSM for treatment is, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, or 64 mg. In an embodiment, the dose of CuPTSM for treatment is, per day, 0.1 mg-64 mg.

In certain embodiments, the dose of CuPTSM for treatment is about, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, or 51 mg. In an embodiment, the dose of CuPTSM for treatment is about, per day, 0.1 mg-51 mg.

In certain embodiments, the dose of CuPTSM for treatment is, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, or 51 mg. In an embodiment, the dose of CuPTSM for treatment is, per day, 0.1 mg-51 mg.

In certain embodiments, the dose of CuPTSM for treatment is about, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, or 39 mg. In an embodiment, the dose of CuPTSM for treatment is about, per day, 0.1 mg-39 mg.

In certain embodiments, the dose of CuPTSM for treatment is, per day, 0.1 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, or 39 mg. In an embodiment, the dose of CuPTSM for treatment is, per day, 0.1 mg-39 mg.

In certain embodiments, the dose of CuPTSM for treatment is about, per day, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, or 26 mg. In an embodiment, the dose of CuPTSM for treatment is about, per day, 1 mg-26 mg.

In certain embodiments, the dose of CuPTSM for treatment is, per day, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, or 26 mg. In an embodiment, the dose of CuPTSM for treatment is, per day, 1 mg-26 mg.

In certain embodiments, the dose of CuPTSM for treatment is about, per day, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, or 26 mg. In an embodiment, the dose of CuPTSM for treatment is about, per day, 5 mg-26 mg.

In certain embodiments, the dose of CuPTSM for treatment is, per day, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, or 26 mg. In an embodiment, the dose of CuPTSM for treatment is, per day, 5 mg-26 mg.

In certain embodiments, the dose of CuPTSM for treatment is about, per day, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is about, per day, 1 mg-20 mg.

In certain embodiments, the dose of CuPTSM for treatment is, per day, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is, per day, 1 mg-20 mg.

In certain embodiments, the dose of CuPTSM for treatment is about, per day, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is about, per day, 5 mg-20 mg.

In certain embodiments, the dose of CuPTSM for treatment is, per day, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is, per day, 5 mg-20 mg.

In certain embodiments, the dose of CuPTSM for treatment is about, per day, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is about, per day, 10 mg-20 mg.

In certain embodiments, the dose of CuPTSM for treatment is, per day, 10 mg, 11 mg, 12 mg, 13 mg, 14 mg, 15 mg, 16 mg, 17 mg, 18 mg, 19 mg, or 20 mg. In an embodiment, the dose of CuPTSM for treatment is, per day, 10 mg-20 mg.

In certain embodiments, the dose of CuPTSM for treatment is about, per day, 10 mg, 11 mg, 12 mg, 13 mg, 14 mg, 15 mg, 16 mg, 17 mg, or 18 mg. In an embodiment, the dose of CuPTSM for treatment is about, per day, 10 mg-18 mg.

In certain embodiments, the dose of CuPTSM for treatment is, per day, 10 mg, 11 mg, 12 mg, 13 mg, 14 mg, 15 mg, 16 mg, 17 mg, or 18 mg. In an embodiment, the dose of CuPTSM for treatment is, per day, 10 mg-18 mg.

In certain embodiments, the dose of CuPTSM for treatment is about, per day, 12 mg, 13 mg, 14 mg, 15 mg, or 16 mg. In an embodiment, the dose of CuPTSM for treatment is about, per day, 12 mg-16 mg.

In certain embodiments, the dose of CuPTSM for treatment is, per day, 12 mg, 13 mg, 14 mg, 15 mg, or 16 mg. In an embodiment, the dose of CuPTSM for treatment is, per day, 12 mg-16 mg.

In certain embodiments, the dose of CuPTSM for treatment is about, per day, 13 mg, 14 mg, or 15 mg. In an embodiment, the dose of CuPTSM for treatment is about, per day, 13 mg-15 mg.

In certain embodiments, the dose of CuPTSM for treatment is, per day, 13 mg, 14 mg, or 15 mg. In an embodiment, the dose of CuPTSM for treatment is, per day, 13 mg-15 mg.

In certain embodiments, the dose of CuPTSM for treatment is about, per day, 14 mg. In certain embodiments, the dose of CuPTSM for treatment is, per day, 14 mg.

In other embodiments, provided herein is a method of treating ALS in a subject in need thereof, wherein the subject is administered a low dose of CuPTSM. The term "low dose" as used herein refers to a dose that is below the therapeutically effective amount of the reference compound CuATSM when administered to treat ALS. In some embodiments, the term "low dose" refers to a dose that is one or more orders of magnitude lower than the therapeutically effective amount of the reference compound CuATSM when administered to treat ALS. In some embodiments, the term "low dose" refers to a dose that is one-half, one-third, one-fourth, one-fifth, one-sixth, one-seventh, one-eighth or less than the therapeutically effective amount of the reference compound CuATSM when administered to treat ALS. In some embodiments, a "low dose" of CuPTSM is within the doses, or dose ranges, described herein. While the amounts of CuPTSM should result in the effective treatment of ALS, the amounts are preferably not excessively toxic to the patient (i.e., the amounts are preferably within toxicity limits as established by medical guidelines). In some embodiments, either to prevent excessive toxicity or provide a more efficacious treatment, or both, of ALS, a limitation on the total administered dosage is provided. Typically, the amounts considered herein are per day; however, half-day and two-day or three-day cycles are also considered herein.

In certain embodiments, the subject in need thereof is treatment naïve. In certain embodiments, the subject in need thereof has received previous treatment for ALS other than CuPTSM that has been inadequate (e.g., assessed by the subject and/or a physician), has been ineffective, and/or has not resulted in a detectable improvement in one or more parameters or symptoms associated with ALS and/or has not caused a biological effect that is correlated with the underlying pathology giving rise to the symptoms of ALS.

In certain embodiments, the subject in need thereof is human, and the human has a genetic mutation associated with ALS, wherein the genetic mutation associated with ALS comprises a mutation in the SOD1 gene.

In an aspect, provided herein is a method for treating or preventing a superoxide dismutase 1 (SOD1) associated neurodegenerative disorder in a subject in need thereof, comprising administering to the subject CuPTSM. In an embodiment, the SOD1 associated neurodegenerative disorder is SOD1-associated amyotrophic lateral sclerosis (ALS).

In certain embodiments, the CuPTSM is administered to the subject in combination with an additional ALS treatment therapy. Current treatment for ALS includes administration of riluzole and edaravone, which have been shown to be modestly effective. Other therapies for ALS include medications to treat specific symptoms associated with the disease, for example muscle relaxants such as baclofen or diazepam may be prescribed to treat muscle cramps, spasms, and spasticity. Gabapentin may be prescribed to help control pain. Such medicines like amitriptyline, trihexyphenidyl, scopaderm, and glycopyrrolate can be administered to treat excess saliva in the mouth due to difficulty swallowing. Medication may also be required for the treatment of constipation, fatigue, depression, difficulty sleeping, and pseudobulbar affect associated with ALS.

In certain embodiments, the CuPTSM is administered at a dose that achieves a plasma Cmax of about 50-650 ng/mL in the subject. The term "Cmax" is defined as the maximum concentration of active CuPTSM or CuATSM achieved in the plasma or spinal cord following administration of the drug.

Pharmaceutical Compositions

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of the CuPTSM, and can generally be estimated based on EC50s found to be effective in in vitro and in vivo animal models. In general, dosage is from 0.01 μg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein CuPTSM is administered in maintenance doses, ranging from 0.01 µg to 100 g/kg of body weight, once or more daily, to once every 20 years.

Different dosage regiments may be used to treat ALS. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

In an aspect, the CuPTSM may be administered alone or in combination with at least one pharmaceutically acceptable excipient. The expression "pharmaceutically acceptable" means acceptable for use in the pharmaceutical and veterinary arts, i.e., not being unacceptably toxic or otherwise unsuitable. Examples of pharmaceutically acceptable adjuvants include diluents, excipients and the like. Reference may be made to "Remington's: The Science and Practice of Pharmacy," 21st Ed., Lippincott Williams and Wilkins, 2005, for guidance on drug formulations generally.

CuPTSM, in pure form or in an appropriate pharmaceutical composition, can be administered via any of the accepted modes of administration or agents known in the art. The CuPTSM can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methylcellulose, and cellulose acetate phthalate; gelatin; talc; stearic acid; magnesium stearate; vegetable oils such as peanut oil, cottonseed oil; sesame oil, olive oil, corn oil, and oil of *theobroma*; propylene glycol, glycerin; sorbitol; polyethylene glycol; water; agar; alginic acid; isotonic saline, and phosphate buffer solutions; as well as other compatible substances normally used in pharmaceutical formulations. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Emulsifiers can include polysorbates, such as TWEEN, for example TWEEN-20 and TWEEN-80. TWEEN-80 is $C_{64}H_{124}O_{26}$, is derived from polyethoxylated sorbitan and oleic acid, and is also referred to as polyoxyethylene (20) sorbitan monooleate and (x)-sorbitan mono-9-octadecenoate poly(oxy-1,2-ethanediyl). Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release CuPTSM in a certain part of the intestinal tract in a delayed manner. Examples of embedded compositions that can be used are polymeric substances and waxes. The CuPTSM also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., CuPTSM, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to 99% by weight of CuPTSM described herein, and 99% to 1% by weight of a pharmaceutically acceptable excipient. In one example, the composition will be between about 5% and about 75% by weight of the CuPTSM described herein, with the rest being suitable pharmaceutical excipients.

In various embodiments, the pharmaceutically composition is for the treatment of ALS in a subject in need thereof.

In various embodiments, the pharmaceutical composition comprises CuPTSM at any of the doses provided herein.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

The invention is further described in detail by reference to the following experimental examples. These examples are included merely for purposes of illustration of certain aspects and embodiments of the present invention, and are not intended to limit the invention. Thus, the invention should in no way be construed as being limited to the following examples, but rather, should be construed to encompass any and all variation which become evident as a result of the teaching provided herein.

EXAMPLES

Example 1—Pharmacokinetics of CuPTSM Compared to CuATSM

The SOD1$^{G93A}$ transgenic mouse model of ALS has been the most widely used animal model since the 1990s. The mouse was genetically engineered to overexpress a mutant form of the human Cu/Zn superoxide dismutase 1 (SOD1) gene harboring an ALS-associated glycine to alanine mutation at amino acid position 93 (G93A). Currently, the clinical strategy for the treatment of ALS with CuATSM is to escalate human dosing until ALS patients show plasma levels equivalent to those seen in mice given 30 mg/kg/day.

Figure 1B:
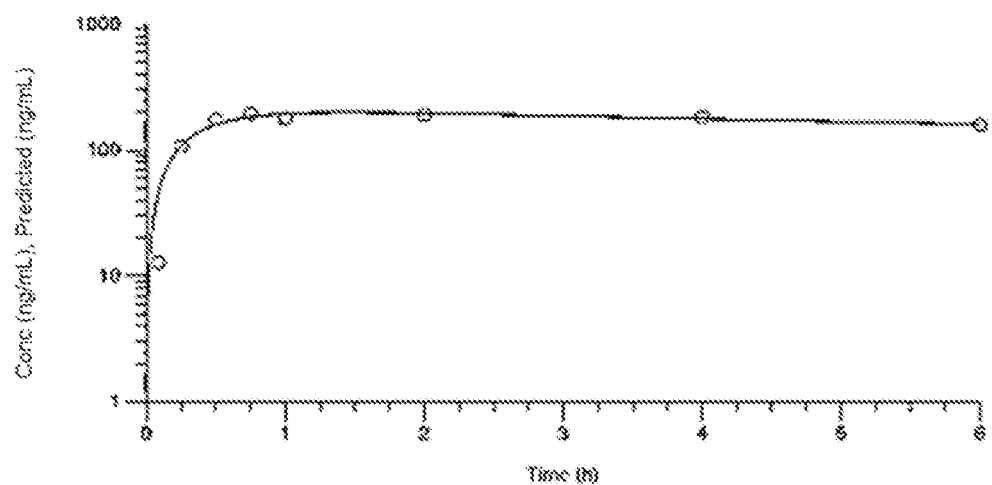
FIG. 1B is a graph depicting plasma concentrations of CuATSM over a period of 6 hr after administration of a single bolus dose of 30 mg/kg.

To compare the effects of CuPTSM to CuATSM in vivo, a single bolus of 30 mg/kg CuPTSM or 30 mg/kg CuATSM in an oral suspension of 0.5% methylcellulose/0.4% TWEEN-80/0.9% normal saline was administered to SOD1$^{G93A}$ mice. Absorption half-life, elimination half-life, and Cmax measurements were taken from both plasma and spinal cord samples to measure drug exposure of CuPTSM or CuATSM for up to 6 hr after administration of drug. A decrease in plasma concentrations of CuPTSM was observed over time (FIG. 1A), with an absorption half-life of 0.54 hr, an elimination half-life of 2.44 hr, and a plasma Cmax of 1565 ng/mL. Plasma concentrations of CuATSM plateaued and remained constant 6 hours after administration (FIG. 1B), with an absorption half-life of 0.24 hr, an elimination half-life of 13.7 hr, and a plasma Cmax of 198 ng/mL.

Figure 2A:
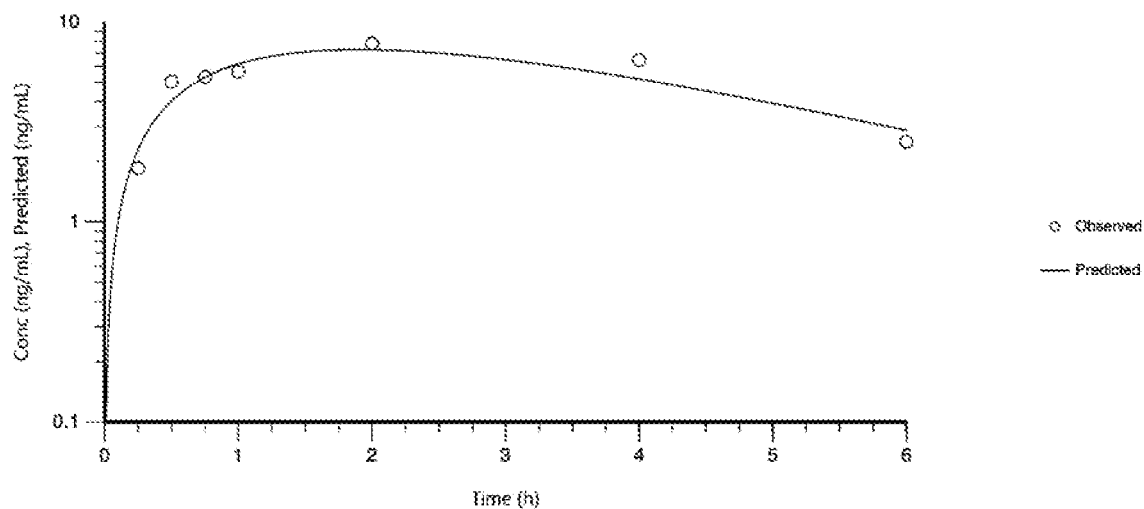
FIG. 2A is a graph depicting the spinal cord concentrations of CuPTSM over a period of 6 hr after administration of a single dose of 30 mg/kg.
Figure 2B:
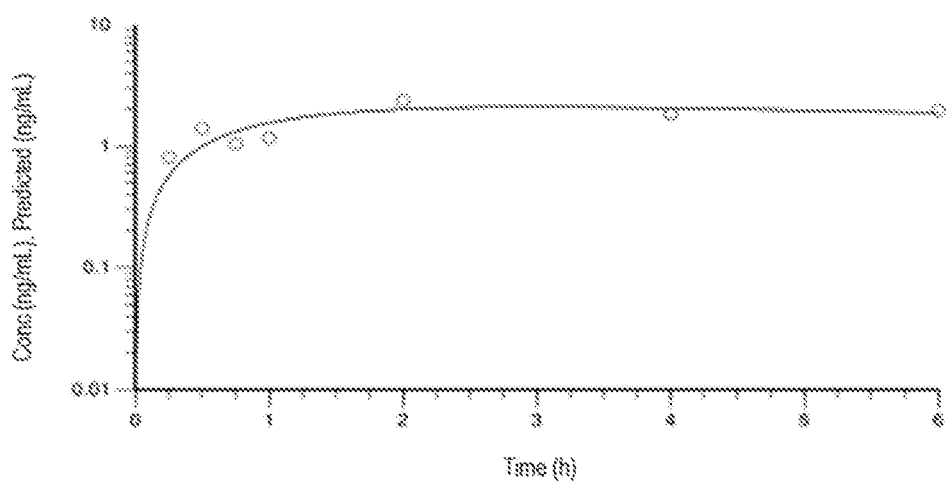
FIG. 2B is a graph depicting spinal cord concentrations of CuATSM over a period of 6 hr after administration of a single bolus dose of 30 mg/kg.

Similar measurements were recorded for concentrations of CuPTSM and CuATSM in the spinal cord. As with the plasma concentrations from the mice administered 30 mg/kg CuPTSM, concentrations decreased over time (FIG. 2A), and the CuPTSM was found to have an absorption half-life of 1.0 hr, an elimination half-life of 1.9 hr, and a Cmax of 7.27 ng/mL. As with the plasma concentrations, the spinal cord concentrations of CuATSM remained constant, even 6 hr after administration (FIG. 2B). In the spinal cord, CuATSM had an absorption half-life of 0.65 hr, an elimination half-life of 13.8, and a Cmax of 2 ng/mL.

Figure 3A:
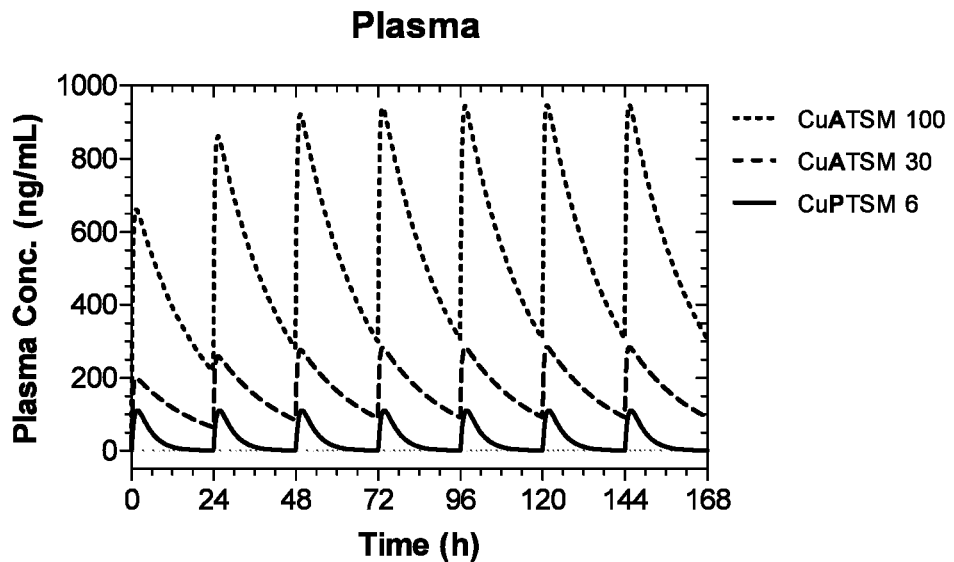
FIG. 3A is a simulation using PK parameters derived from the experiment of FIG. 1A and FIG. 1B, assuming linear pharmacokinetics. Plasma concentrations (ng/mL) in mice receiving 6 mg/kg CuPTSM, 30 mg/kg CuATSM, or 100 mg/kg CuATSM are depicted over time (hours).
Figure 3B:
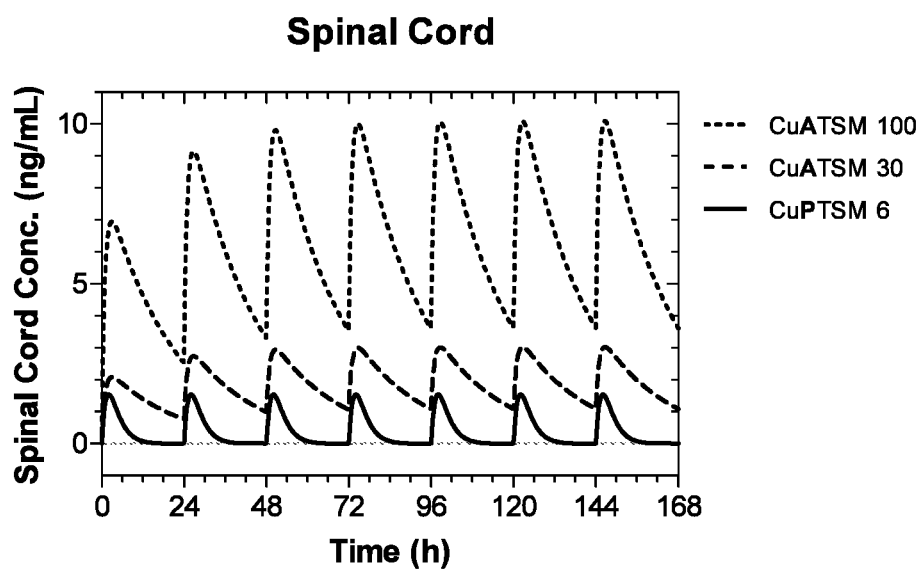
FIG. 3B is a simulation using PK parameters derived from the experiment of FIG. 1A and FIG. 1B, assuming linear pharmacokinetics. Spinal cord concentrations (ng/mL) in mice receiving 6 mg/kg CuPTSM, 30 mg/kg CuATSM, or 100 mg/kg CuATSM are depicted over time (hours).

Using the data and parameters derived from the above experiments using a single bolus of 6 mg/kg CuPTSM, 30 mg/kg CuATSM, or 100 mg/kg CuATSM, plasma and spinal cord concentrations were recorded on a plot over time (hours) to illustrate pharmacokinetic simulations over time. Linear kinetics were assumed. Previous studies using CuPTSM demonstrated that while 30 mg/kg of CuATSM is well-tolerated by mice, CuPTSM at the same dosing is toxic to mice. Plasma concentrations of 30 mg/kg CuATSM and 100 mg/kg CuATSM did not return to 0 ng/mL prior the next dose. In contrast, the CuPTSM plasma concentration levels increased after administering 6 mg/kg to the mice, and plasma levels returned to 0 ng/mL prior to the next dose (FIG. 3A). Similar results were obtained when concentrations were measured in spinal cord samples (FIG. 3B).

Example 2—Efficacy of CuPTSM in SOD1$^{G93A}$ Mice

Figure 4A:
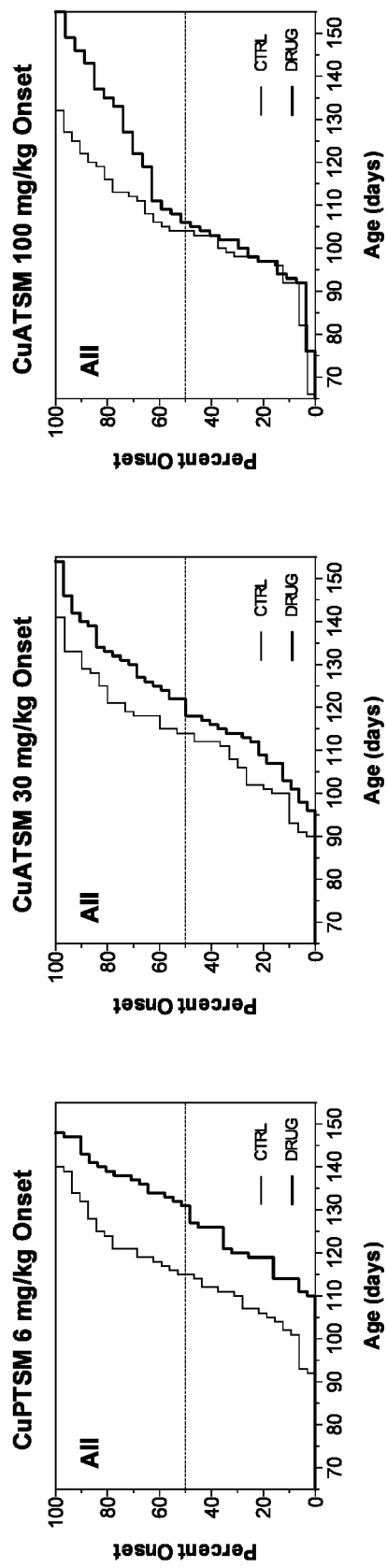
FIG. 4A is a set of plots depicting the percentage of the populations experiencing onset of paresis throughout the study.
Figure 4B:
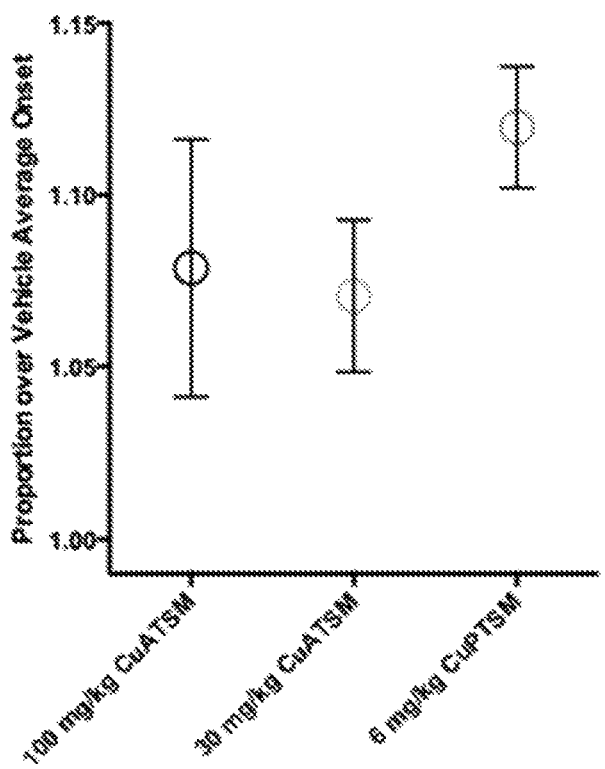
FIG. 4B illustrates the efficacy of 6 mg/kg CuPTSM, 30 mg/kg CuATSM, or 100 mg/kg CuATSM as measured by onset of paresis compared to mice given vehicle only.

To test the efficacy of CuPTSM compared to CuATSM, mice were tested for delays in paresis and overall lifespan. Mice were given 6 mg/kg CuPTSM (n=32), 30 mg/kg CuATSM (n=32), and 100 mg/kg CuATSM (n=32) once a day to assess disease progression, and identify drug-induced changes in SOD1$^{G93A}$ mice compared to their respective vehicle-only control mice. Neurological scoring to test the onset of paresis for each mouse was performed throughout the study according to the protocol as disclosed in Hatzipetros et al. (2015, J. Visualized Experiments. doi:10.3791/53257), incorporated herein by reference in its entirety. Briefly, mice were scored on a scale of NS 0 (pre-symptomatic) to NS 4 (humane end-point) based on a combination of a tail suspension test, a walking test, and a "righting reflex" test. Onset of paresis was measured throughout the study (FIG. 4A), with either CuPTSM or CuATSM delaying onset over the control. However, when each experimental group was compared to its respective control group, the mice administered 6 mg/kg CuPTSM significantly delayed onset of paresis over CuATSM at either the 30 mg/kg dose or the CuATSM 100 mg/kg group over their respective control groups (FIG. 4B).

Figure 5A:
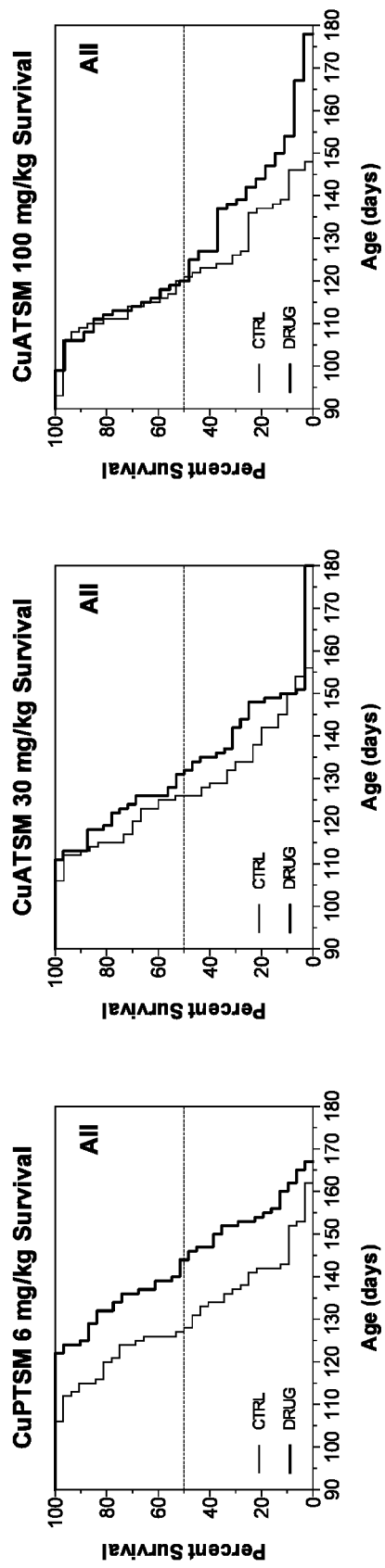
FIG. 5A is a set of plots tracking the percent survival of each treatment population throughout the study.
Figure 5B:
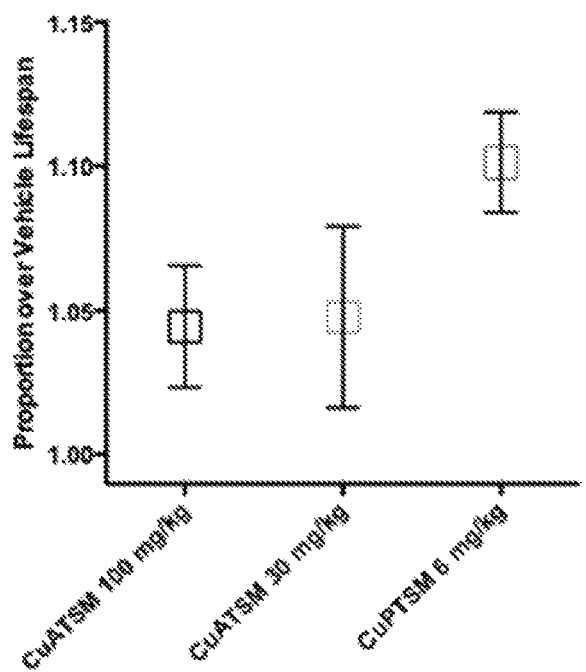
FIG. 5B illustrates the lifespan of mice given 6 mg/kg CuPTSm, 30 mg/kg CuATSM, or 100 mg/kg CuATSM over those receiving vehicle.

Survival for each cohort was also tracked throughout the study. As with the paresis study, mice administered 6 mg/kg CuPTSM, 30 mg/kg CuATSM, or 100 mg/kg CuATSM demonstrated an increase in survival over the control counterparts (FIG. 5A). When the experimental groups were compared to one another, the cohort treated with CuPTSM had markedly improved survival over the groups treated with either dose of CuATSM (FIG. 5B).

Figure 6A:
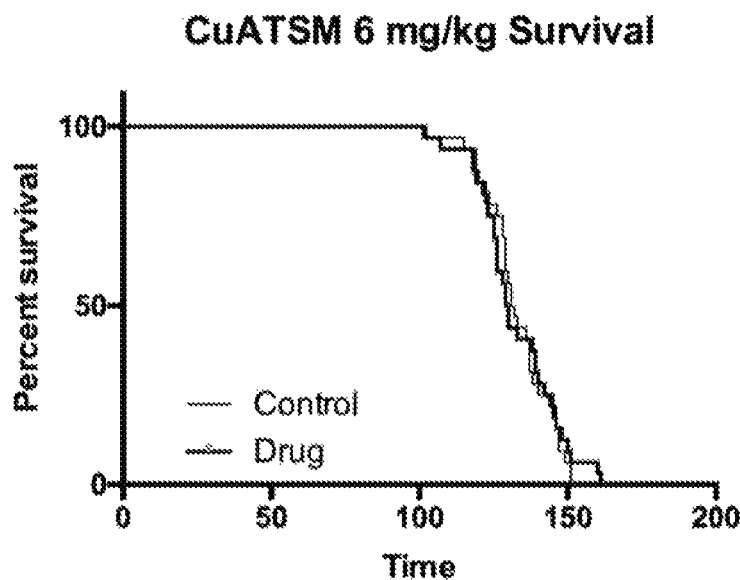
FIG. 6A is a plot of percent survival over time of mice given 6 mg/kg CuATSM compared to a control cohort of mice.
Figure 6B:
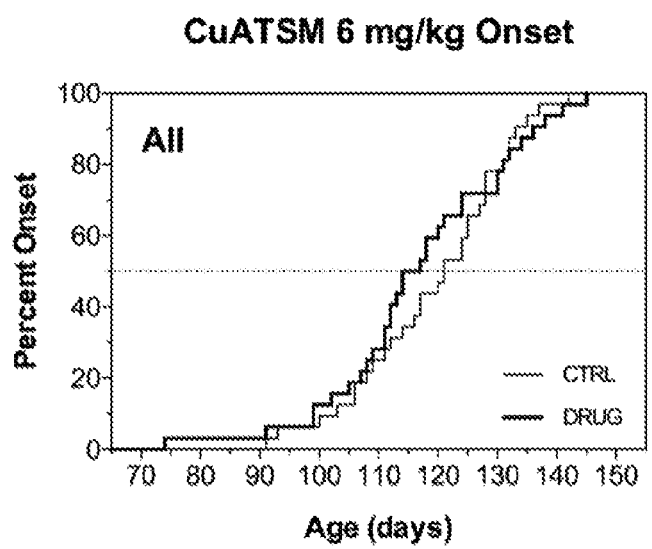
FIG. 6B is a plot illustrating the percentage of the population of mice experiencing onset of paresis given 6 mg/kg CuATSM compared to control.

To compare the effects of CuPTSM administered at a much lower dose than CuATSM, mice were administered 6 mg/kg CuATSM and survival and onset of paresis were measured as before. The population of mice that received the 6 mg/kg CuATSM experienced no significant difference in survival when compared to the control mice (FIG. 6A). Similarly, no significant improvement in onset of paresis was seen with administration of 6 mg/kg CuATSM compared to control (FIG. 6B).

Compound muscle action potential (CMAP) was measured in mice given CuPTSM, CuATSM, or vehicle. CMAP is an electrophysiological technique that assess functional integrity of motor axons. The sciatic nerve is stimulated using implanted microelectrodes proving small electrical currents, and the response is measured in the innervated tibialis anterior (TA) muscle using an implanted recording electrode. It is known that the CMAP signal is decreased in the case of neuromuscular diseases, like in ALS patients, and recapitulated in the SOD1$^{G93A}$ mouse model due to motor unit loss. In male SOD1$^{G93A}$ mice, it has been shown that CMAP changes may happen as early as age day 50 and invariably worse after. In the present study, mice were treated once a day for 14 days with 2, 6, or 12 mg/kg CuPTSM; 10 or 30 mg/kg CuATSM; or vehicle (control). A total of 9 male mice were tested for each condition.

Figure 7A:
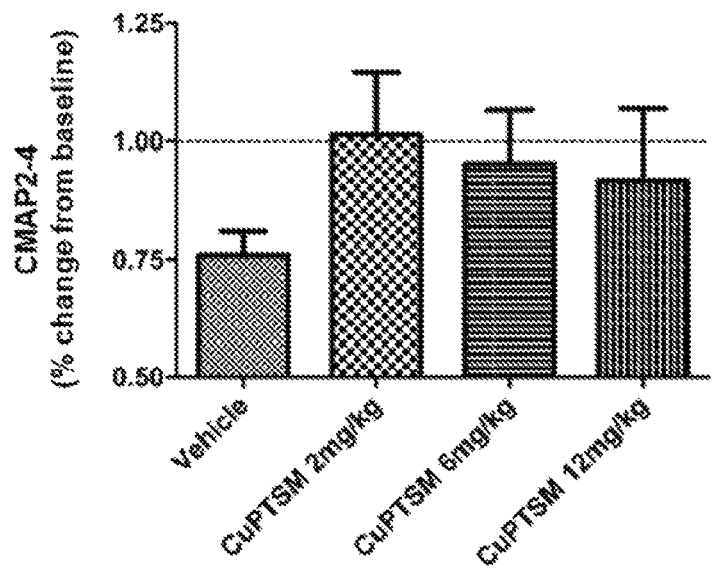
FIG. 7A illustrates differences in compound muscle action potential (CMAP) measurements between male mice given 2, 6, or 12 mg/kg CuPTSM compared to vehicle.
Figure 7B:
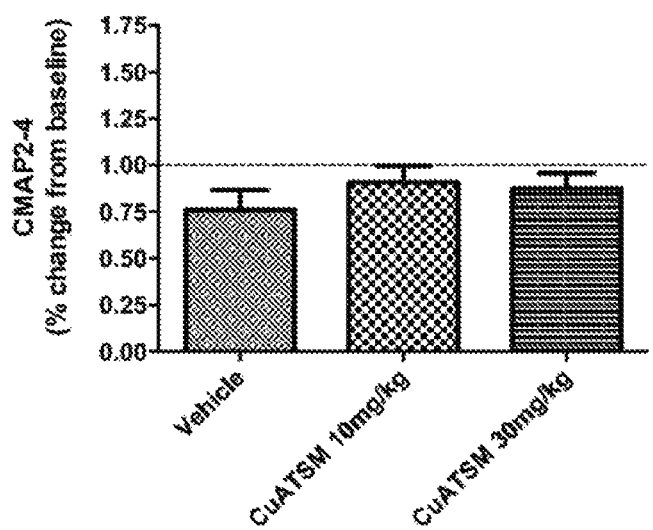
FIG. 7B illustrates differences in CMAP measurements between mice treated with 10 or 30 mg/kg CuATSM and mice treated with vehicle.

Prior to drug administration and assignment of mice to a cohort, CMAP was recorded for each mouse to establish a baseline measurement. Mice were then randomized into each treatment cohort, and administered the respective compounds and dosages of the cohort via oral gavage daily for two weeks. CMAP data was recorded at the end of the two weeks, and compared to the baseline measurements to calculate percent of baseline to illustrate the efficacy of CuPTSM and CuATSM compared to just vehicle. Male mice administered CuPTSM demonstrated a significantly greater change from baseline at all doses over the mice treated with just the vehicle (FIG. 7A). The cohorts of mice treated with 10 mg/kg or 30 mg/kg CuATSM experienced no significant difference in CMAP measurements over the mice treated with vehicle (FIG. 7B).

Considering the data, CuPTSM was surprisingly more efficacious at delaying paresis, improving survival, and protecting the functional integrity of motor axons than CuATSM, despite markedly less drug exposure, as measured by pharmacokinetics.

The invention claimed is:
1. A method of treating amyotrophic lateral sclerosis (ALS) in a subject in need thereof, the method comprising administering to the subject a therapeutically effective amount of CuPTSM, having the formula:

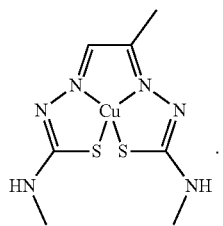

2. The method of claim 1, wherein the ALS is familial or sporadic.

3. The method of claim 1, wherein the subject in need thereof is treatment naïve.

4. The method of claim 1, wherein the subject in need thereof has received previous treatment for ALS.

5. The method of claim 1, wherein the therapeutically effective dose of CuPTSM is 0.01 mg/kg/day-12 mg/kg/day.

6. The method of claim 1, wherein the subject in need thereof is human, and the human has a genetic mutation associated with ALS.

7. The method of claim 6, wherein the genetic mutation associated with ALS comprises a mutation in the SOD1 gene.

8. The method of claim 1, wherein the CuPTSM is administered to the subject in combination with an additional ALS treatment therapy.

9. The method of claim 8, wherein the CuPTSM is administered at a dose that achieves a plasma Cmax of about 50-640 ng/mL in the subject.

10. A pharmaceutical composition comprising CuPTSM and a pharmaceutically acceptable excipient, wherein the CuPTSM has the formula:

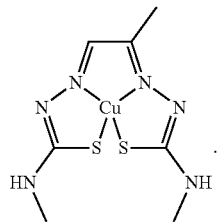

11. The pharmaceutical composition of claim 10, wherein the pharmaceutically acceptable excipient comprises cellulose and a surfactant.

12. The pharmaceutical composition of claim 11, wherein the cellulose is methylcellulose.

13. The pharmaceutical composition of claim 11, wherein the surfactant is a polysorbate.

14. The pharmaceutical composition of claim 13, wherein the polysorbate is polyoxyethylene (20) sorbitan monooleate.

* * * * *